(12) United States Patent
Koike et al.

(10) Patent No.: US 7,749,442 B2
(45) Date of Patent: Jul. 6, 2010

(54) SAMPLE MEASURING DEVICE

(75) Inventors: Masufumi Koike, Kyoto (JP); Satoru Mizutani, Kyoto (JP)

(73) Assignee: ARKRAY, Inc., Kyoto-shi (JP)

( * ) Notice: Subject to any disclaimer, the term of this patent is extended or adjusted under 35 U.S.C. 154(b) by 1168 days.

(21) Appl. No.: 10/498,782

(22) PCT Filed: Dec. 16, 2002

(86) PCT No.: PCT/JP02/13137

§ 371 (c)(1),
(2), (4) Date: Jun. 10, 2004

(87) PCT Pub. No.: WO03/052427

PCT Pub. Date: Jun. 26, 2003

(65) Prior Publication Data

US 2005/0123447 A1    Jun. 9, 2005

(30) Foreign Application Priority Data

Dec. 14, 2001 (JP) ............................. 2001-381606
Dec. 14, 2001 (JP) ............................. 2001-381607

(51) Int. Cl.
*G01N 33/00* (2006.01)
(52) U.S. Cl. .................... 422/68.1; 422/82.05; 422/99; 422/100
(58) Field of Classification Search .................. 435/24, 435/4, 32; 422/68.01, 82.05, 99, 100
See application file for complete search history.

(56) References Cited

U.S. PATENT DOCUMENTS 4,690,899 A    9/1987  Klose et al.

(Continued)

FOREIGN PATENT DOCUMENTS

EP    0803288    10/1997

(Continued)

OTHER PUBLICATIONS

First Office Action issued in the corresponding Chinese Patent Application No. 02827958.1 dated Feb. 15, 2008.

(Continued)

*Primary Examiner*—Sam P Siefke
(74) *Attorney, Agent, or Firm*—Knobbe Martens Olson & Bear LLP

(57) ABSTRACT

The present invention provides a sample measuring device capable of allowing not only one but more than one kind of samples to react with a reagent, and enhancing a reliability in photometric analysis accuracy by reliably mixing and agitating the sample and the reagent prior to the photometric analysis. The device includes a reagent melting/mixing means, a sample supply chamber positioned on the upstream side of, and communicating with, the reagent melting/mixing means when the sample is allowed to flow into the reagent melting/mixing means, and at least one measuring chamber positioned on the downstream side of, and communicating with, the reagent melting/mixing means, wherein the sample supply chamber, the reagent melting/mixing means, and the measuring chamber are arranged sequentially from the upstream to the downstream directions of the flow passage, with the sample supply chamber positioned on the upstream side with respect to the sample flow by a sample moving means. When a centrifugal machine is used as a reagent moving means and the sample measuring device is installed and used with its imaginary axis kept along the radial direction of a rotor of the centrifugal machine, the sample supply chamber can be provided to be positioned on the radially inner side of the rotor in the centrifugal machine.

35 Claims, 12 Drawing Sheets

U.S. PATENT DOCUMENTS

| | | |
|---|---|---|
| 4,961,915 A | 10/1990 | Martin |
| 5,693,233 A | 12/1997 | Schembri |
| 6,063,589 A * | 5/2000 | Kellogg et al. ............ 435/24 |
| 6,123,119 A | 9/2000 | Okumura |
| 6,153,148 A | 11/2000 | Thomas |
| 6,180,062 B1 * | 1/2001 | Naka et al. ............ 422/81 |
| 6,458,325 B1 * | 10/2002 | Roscher et al. ............ 422/68.1 |

FOREIGN PATENT DOCUMENTS

| | | |
|---|---|---|
| JP | 61-193072 | 8/1986 |
| JP | 3223674 | 10/1991 |
| JP | 10-132712 | 5/1998 |
| WO | WO 95/06870 | 3/1995 |
| WO | WO 95/33986 | 12/1995 |
| WO | WO 97/02357 | 1/1997 |
| WO | WO 97/21090 | 6/1997 |
| WO | WO 97/39338 | 10/1997 |
| WO | WO 98/13684 | 4/1998 |
| WO | WO 98/49548 | 11/1998 |
| WO | WO 98/53311 | 11/1998 |
| WO | WO 99/05512 | 2/1999 |
| WO | WO 99/09042 | 2/1999 |
| WO | WO 99/33559 | 7/1999 |
| WO | WO 00/69560 | 11/2000 |
| WO | WO 00/72970 A1 | 12/2000 |

OTHER PUBLICATIONS

Notice of Reason for Rejection for Japanese Patent Application No. 2003-553265 mailed Aug. 5, 2008 by Japanese Patent Office.

* cited by examiner

SAMPLE MEASURING DEVICE

TECHNICAL FIELD

The present invention relates to a sample measuring device, and more specifically to a sample measuring device which can be suitably used when, for example, optically measuring the properties of a reaction product obtained by mixing a reagent with blood plasma, biological liquid, or the like for reaction.

BACKGROUND ART

An apparatus for analyzing blood plasma, biological liquid or the like is already well-known, as disclosed in JP 10-501340 A (PCT), etc. In the "Modified Siphons for Improved Metering Precision" disclosed in the above-mentioned publication, the rotor of a centrifugal separator is equipped with a blood application chamber, a blood plasma measuring chamber, a retention chamber, a diluting agent measuring chamber, a mixing chamber, a measurement cuvette, etc.; in particular, the blood plasma measuring chamber and the mixing chamber communicate with each other through a siphon, wherein the positional relationship between the siphon inlet communicating with the blood plasma measuring chamber and the siphon outlet communicating with the mixing chamber is such that the inlet is situated outward of the outlet with respect to the radial direction of the rotor.

According to the invention disclosed in the PCT publication, when the rotor rotates, blood contained in the blood application chamber is moved by the centrifugal force to the blood plasma measuring chamber, where it is separated into cells and blood plasma. At the same time, the diluting agent contained in the retention chamber is moved by the centrifugal force to the diluting agent measuring chamber, and a portion of the diluting agent enters the mixing chamber from the diluting agent measuring chamber through a siphon.

The blood plasma separated from the cells in the blood plasma measuring chamber enters the mixing chamber through a siphon to be mixed with a diluting agent. The blood plasma that has been mixed with the diluting agent in the mixing chamber is distributed through a distribution ring to a large number of measurement cuvettes arranged in the circumferential direction of the rotor. Each of these measurement cuvettes, to which the diluted blood plasma is distributed, contains a reagent, which reacts with the blood plasma allowed to flow in and is finally subjected to photometric analysis.

The above-described invention disclosed in the above publication has a problem in that the measurement cuvettes subjected to photomeric analysis are previously provided with a reagent, which means only one kind of reagent is used for reaction with the diluted blood plasma.

Further, when the diluted blood plasma reacts with the reagent upon entering the measurement cuvettes containing the reagent, practically no agitating action is exerted, so that the reliability in the photometric analysis of the solutions in the measurement cuvettes is rather low.

The present invention has been made with a view toward solving the above problems in the prior art. It is an object of the present invention to provide a sample measuring device which allows a sample to successively react with one or more kinds of reagents, which reliably mixes and agitates the sample and the reagents prior to photometric analysis to thereby achieve high reliability in photometric analysis, and which is simple in construction and easily to handle.

DISCLOSURE OF THE INVENTION

The present invention employs the following means to solve the above-described problems. That is, there is provided a sample measuring device including: one or a plurality of reagent melting/mixing means; a sample supply chamber communicating with the reagent melting/mixing means to cause a sample to flow into the reagent melting/mixing means; and at least one measuring chamber communicating with the reagent melting/mixing means, characterized in that the sample supply chamber, the reagent melting/mixing means, and the measuring chamber are arranged from an upstream to a downstream side of a flow passage for a sample, which is moved by a sample moving means, and that the sample supply chamber is arranged on an upstream side of the reagent melting/mixing means, and the measuring chamber is arranged on a downstream side of the reagent melting/mixing means.

In the above sample measuring device, communication is established between the reagent melting/mixing means and the measuring chamber and, when there are a plurality of reagent melting/mixing means, they are arranged in series, whereby communication is established between the reagent melting/mixing means and the measuring chamber on the downstream side thereof. Thus, it is possible to cause the sample to successively react with not only one but also more than one kind of reagents. Further, the sample and the reagents are reliably mixed and agitated together prior to photometric analysis, thereby achieving an improvement in the reliability of the photometric analysis.

Here, it is to be noted that when it is said that the sample supply chamber, the reagent melting/mixing means, and the measuring chamber are arranged from the upstream to the downstream side in the flow passage of the sample, it means that these components are arranged so that the sample may flow through a fixed route from the upstream to the downstream side, and it does not necessarily mean that these components are arranged in order in a predetermined direction. In other words, if the flow passage is bent, the positional relationship between the chambers may be varied accordingly.

The reagents used in the conventional devices are freeze-dried ones. A freeze-dried reagent requires the production steps of freezing, vacuum drying, etc., resulting in a rather high production cost. In contrast, the present invention allows use of a coating reagent, which can be obtained at low production cost.

As the sample moving means, it is possible to use a centrifugal machine; the sample supply chamber, the reagent melting/mixing means, and the measuring chamber can be arranged in order along the radial direction of the rotor of the centrifugal machine, and the sample supply chamber can be installed in the centrifugal machine so as to be situated on the inner side in the radial direction of the rotor. In this case, it is possible to establish communication between a plurality of reagent melting/mixing means through siphons; further, the reagent melting/mixing means can be formed by a reagent melting chamber containing a reagent to be caused to react with the sample and a mixing chamber communicating with this sample melting chamber through a siphon.

When using a centrifugal machine, it is most desirable for the sample supply chamber, the reagent melting/mixing means, and the measuring chamber to be arranged in the stated order from the upstream to the downstream side of the sample flow passage without involving any inversion.

Further, the reagent moving means may consist of a pressure generating means; for example, it is possible to move the reagent through suction or pressurization by a pump means.

In such cases, it is desirable to provide a liquid flow control means equipped with a valve body and a sample detecting means.

In the sample measuring device according to the prevent invention, there may be formed a bypass passage bypassing at least one of the following components provided between the sample supply chamber and the measuring chamber; the reagent melting chamber, the mixing chamber, and the reagent melting/mixing means including the reagent melting chamber and the mixing chamber.

A construction may be adopted in which, when an action force causing the sample to flow from the sample supply chamber to the measuring chamber is imparted to the sample measuring device, there is generated a time lag in sample inflow into the measuring chamber such that, as compared with the flow passage which allows the sample from the sample supply chamber to reach the measuring chamber through the reagent melting/mixing means, the flow passage which allows the sample to reach the measuring chamber through the bypass communication passage causes the sample to flow into the measuring chamber through the bypass passage before the sample from the sample supply chamber reaches the measuring chamber through the reagent melting/mixing means.

By providing such a bypass passage, a time lag is generated between the time it takes the sample to reach the measuring chamber from the sample supply chamber through the reagent melting/mixing means and the time it takes the sample to directly flow into the measuring chamber by way of this bypass passage, whereby it is possible to previously measure a sample blank in the measuring chamber.

In this way, it is possible to measure the sample blank in the measuring chamber, that is, the cuvette, for performing measurement on the sample that is to react with the reagent, and it is possible to perform sample blank correction without any inter-cuvette difference on a sample that will affect the measurement value, such as a chyle specimen or a hemolysis specimen, whereby it is possible to obtain a more accurate measurement value.

It is desirable for the flow passage to be equipped with at least one back-flow preventing means.

In the present invention, there may be provided at least two measuring chambers, one of which is a measuring chamber dedicated to sample blank measurement communicating with the sample supply chamber so as to bypass one or a plurality of reagent melting/mixing means; the other measuring chamber can be provided so as to communicate with the sample supply chamber through one or a plurality of reagent melting/mixing means.

The properties of the reaction sample flowing into the measuring chambers are usually measured by an optical measuring means or an electro-chemical measuring means.

Further, it is possible to provide an air vent hole at least in the reagent melting/mixing means. Due to this air vent hole, it is possible to move the sample smoothly to the downstream side.

In the case in which there are provided two measuring chambers, it is possible to provide a measuring chamber with a small cell length and a measuring chamber with a large cell length, whereby, even if the concentration of the sample is high and saturation occurs in the measurement chamber with a small cell length to make measurement impossible, measurement is possible in the measuring chamber with a large cell length.

Further, in the sample measuring device of the present invention, it is possible to provide an overflow chamber communicating with the measuring chamber. This overflow chamber is provided so as to be situated on the downstream side of the chamber adjacent to and on the upstream side of the measuring chamber.

Further, it is also possible to provide a disposal chamber communicating with the measuring chamber. This disposal chamber is provided so as to be situated on the downstream side of the measuring chamber.

When this sample measuring device is arranged in the rotor of a centrifugal machine to impart a centrifugal force thereto, the above-mentioned overflow chamber is situated so as to be in the centrifugal direction as seen from the chamber next to and on the upstream side of the measuring chamber.

When this disposal sample measuring device is arranged in the rotor of a centrifugal machine to impart a centrifugal force thereto, the above-mentioned disposal chamber is situated so as to be in the centrifugal direction as seen from the measuring chamber.

As described above, in accordance with the present invention, communication is established between the reagent melting/mixing means and the measuring chamber (in the case in which there are provided a plurality of reagent melting/mixing means, these are caused to communicate with each other in series, with the reagent melting/mixing means on the downstream side communicating with the measuring chamber), so that it is possible to cause a sample to react with one or more kinds of reagent.

Further, the sample and the reagent are reliably mixed and agitated together prior to photometric analysis to thereby achieve high reliability in photometric analysis, and it is possible to provide a superior sample measuring device which is of simple construction and which can be produced at low cost and handled easily.

BEST MODE FOR CARRYING OUT THE INVENTION

Embodiment 1

In the following, a sample measuring device according to Embodiment 1 of the present invention will be described in detail with reference to the relevant drawings.

Figure 1:
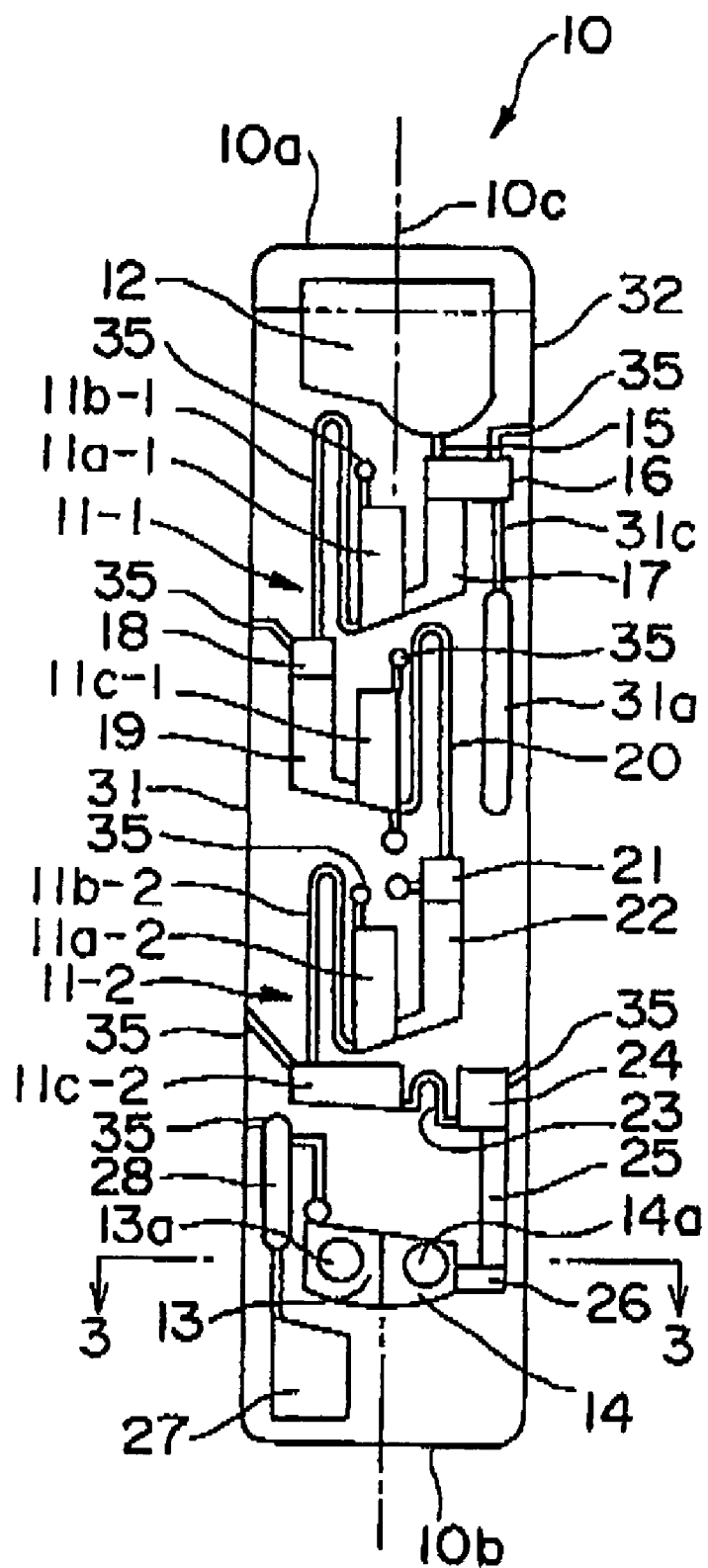
FIG. 1 is a plan view of a sample measuring device according to Embodiment 1.
Figure 2:
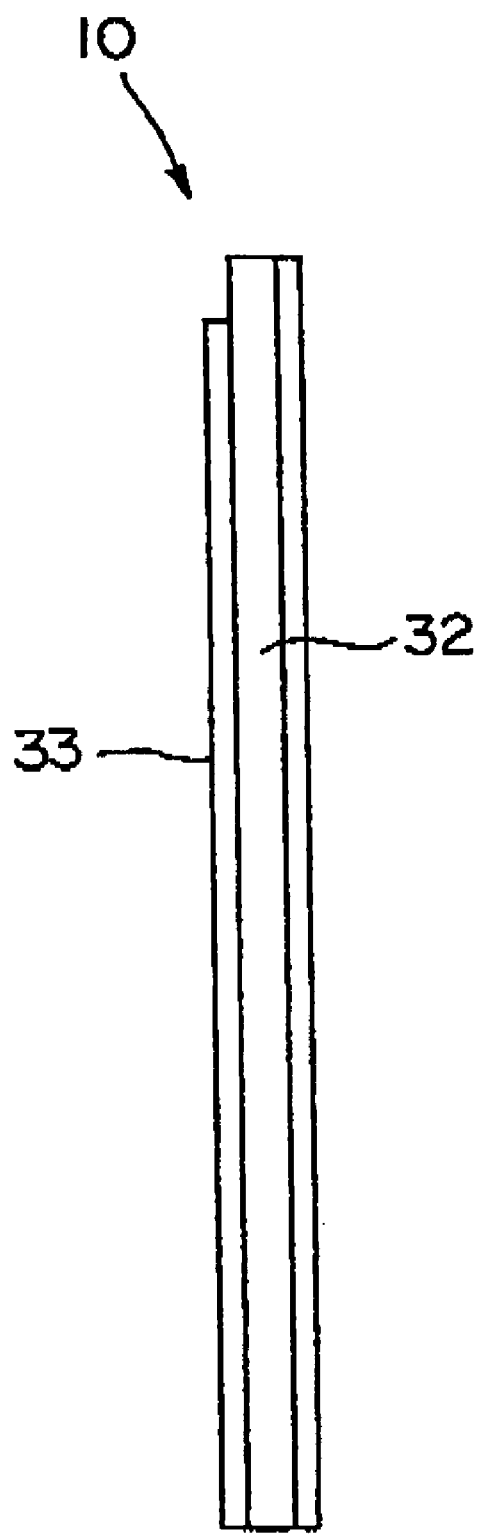
FIG. 2 is a side view of the sample measuring device of Embodiment 1.

FIGS. 1 and 2 show a sample measuring device 10 according to an embodiment of the present invention. As is apparent from FIGS. 1 and 2, which are a plan view and a side view, respectively, the sample measuring device 10 of this embodiment is generally formed as a thin and narrow plate, one surface of which is equipped with first and second reagent melting/mixing means 11-1 and 11-2.

Here, the upper and lower sides of the sample measuring device 10 as seen in the drawing will be referred to as the upstream and downstream sides, respectively, with respect to the sample flowing direction.

While it is possible, in the sample measuring device of the present invention, to provide only one reagent melting/mixing means, this embodiment is equipped, as stated above, with two reagent melting/mixing means (the first reagent melting/mixing means 11-1 and the second reagent melting/mixing means 11-2) which communicate with each other through a siphon and into which a sample flows in successively.

The first reagent melting/mixing means 11-1 situated on the upstream side communicates with a sample supply chamber 12 situates further upstream. The second reagent melting/mixing means 11-2 situated on the downstream side communicates with two measuring chambers 13 and 14 situated further downstream.

The sample supply chamber 12, the first and second reagent melting/mixing means 11-1 and 11-2, and the measuring chambers 13 and 14 are arranged in the direction of the longitudinal central axis 10c of the sample measuring device 10, which is thin and narrow.

The expression: "arranged in the direction of the longitudinal central axis 10c of the sample measuring device 10" does not mean, as is apparent from FIG. 1, that the sample supply chamber 12, the first and second reagent melting/mixing means 11-1 and 11-2, etc. are aligned in the longitudinal central axis 10c, but means that the main formation positions for the sample supply chamber 12, the first and second reagent melting/mixing means 11-1 and 11-2, and the measuring chambers 13 and 14 are successively deviated from each other solely in the direction in which the longitudinal central axis 10c extends.

Figure 5:
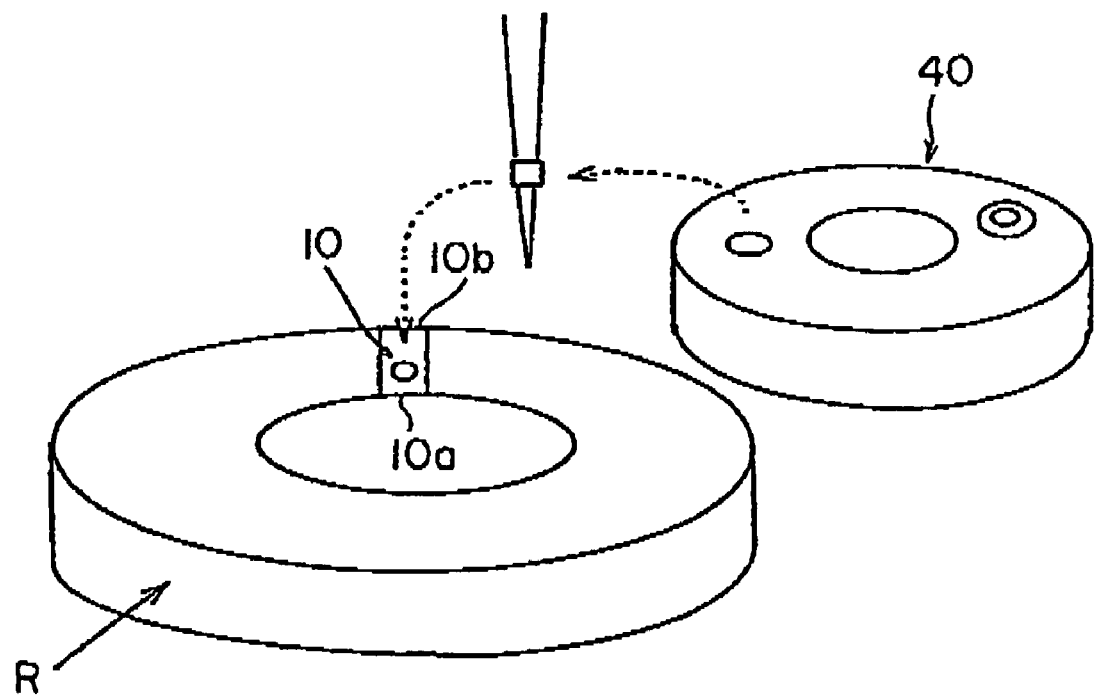
FIG. 5 is a schematic perspective view showing how a sample measuring device is installed in the rotor of a centrifugal machine and how a specimen is supplied from a dispenser to a sample supply chamber of the sample measuring device.

As shown in FIG. 5, when it is to be put to use, the sample measuring device 10 is installed in the rotor R of a centrifugal machine (not shown) such that its longitudinal axis 10c extends along the radial direction of the rotor.

In view of this manner of use, the sample supply chamber 12 is provided at one end 10a to be situated on the radially inner side when the sample measuring device 10 is installed in the rotor R.

That is, when the rotor R is rotated, with the sample measuring device 10 installed therein, there is naturally generated a centrifugal force directed from one end 10a to the other end 10b, opposite thereto, of the sample measuring device 10. Thus, in the following description, the term "centrifugal direction" refers to the direction from one end 10a to the other end 10b of the sample measuring device 10.

The sample supply chamber 12, provided at one end 10a of the sample measuring device 10, communicates with a first back-flow preventing chamber 16 through a tubule 15, and the first back-flow preventing chamber 16 communicates with the first reagent melting/mixing means 11-1 through a passage 17. The first reagent melting/mixing means 11-1 has substantially the same construction as the second reagent melting/mixing means 11-2 described below; more specifically, it is composed of a reagent melting chamber 11a-1 and a mixing chamber 11c-1 communicating with the reagent melting chamber 11a-1 through a siphon 11b-1.

Specifically, communication between the passage 17 and the first reagent melting/mixing means 11-1 is established by connecting the passage 17 to a side end portion in the centrifugal direction of the reagent melting chamber 11a-1 forming the first reagent melting/mixing means 11-1.

Next, the construction of the first reagent melting/mixing means 11-1 will be described in more detail; connected to the end in the centrifugal direction of the reagent melting chamber 11a-1 is the inlet of a siphon tubule forming the siphon 11b-1; this siphon tubule extends along the reagent melting chamber 11a-1 in the direction opposite to the centrifugal direction to be turned up at a position beyond the reagent melting chamber 11a-1 to extend in the centrifugal direction again, thereby forming a U-shaped structure.

In the sample measuring device 10 of this embodiment, in the first reagent melting/mixing means 11-1 on one hand, the outlet of the siphon tubule communicates with the mixing chamber 11c-1 through a second back-flow preventing chamber 18 and a passage 19. Alternatively, on the other hand as in the second reagent melting/mixing means 11-2, it may be formed so as to directly communicate with a second mixing chamber 11c-2.

The first reagent melting/mixing means 11-1 communicates with a third back-flow preventing chamber 21 through a second siphon 20 formed in a similar fashion as the siphon 11b-1 described above, and the third back-flow preventing chamber 21 communicates with the second reagent melting/mixing means 11-2 through a passage 22. More specifically, the inlet of the siphon tubule forming the second siphon 20 is connected to the end in the centrifugal direction of the mixing chamber 11c-1 forming the first reagent melting/mixing means 11-1, and this siphon tubule extends in the direction opposite to the centrifugal direction to be turned up at a position beyond the mixing chamber 11c-1 to extend in the centrifugal direction again, thereby forming a U-shaped structure.

Then, the outlet of the siphon tubule communicates with the third back-flow preventing chamber 21, and the third back-flow preventing chamber 21, in turn, communicates through a passage 22 with the end in the centrifugal direction of the second reagent melting chamber 11a-2 of the second reagent melting/mixing means 11-2. The second mixing chamber 11c-2 forming the second reagent melting/mixing means 11-2 communicates with the two measuring chambers 13 and 14 successively through a reverse-U-shaped tubule 23, a fourth back-flow preventing chamber 24, a passage 25, and a fifth back-flow preventing chamber 26.

Figure 4:
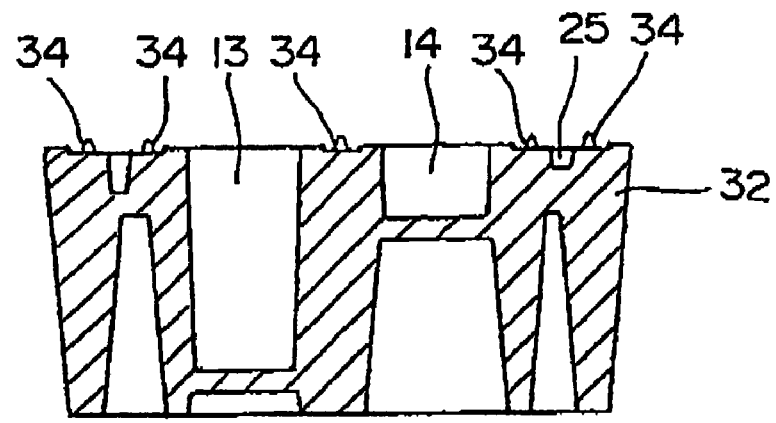
FIG. 4 is a sectional view of the sample measuring device of FIG. 3, taken along the line 3-3.

As is apparent from the sectional view of FIG. 4, the measuring chambers 13 and 14 differ from each other in depth, the so-called cell length of the former being large, and that of the latter being small. The measuring chambers 13 and 14 communicate with each other through a communication means (not shown). As the communication means, various constructions may be possible; for example, the communication passage may be branched off before entering the two measuring chambers to join again after leaving the measuring chambers; alternatively, the two measuring chambers may be formed substantially as a single stepped chamber.

Figure 6:
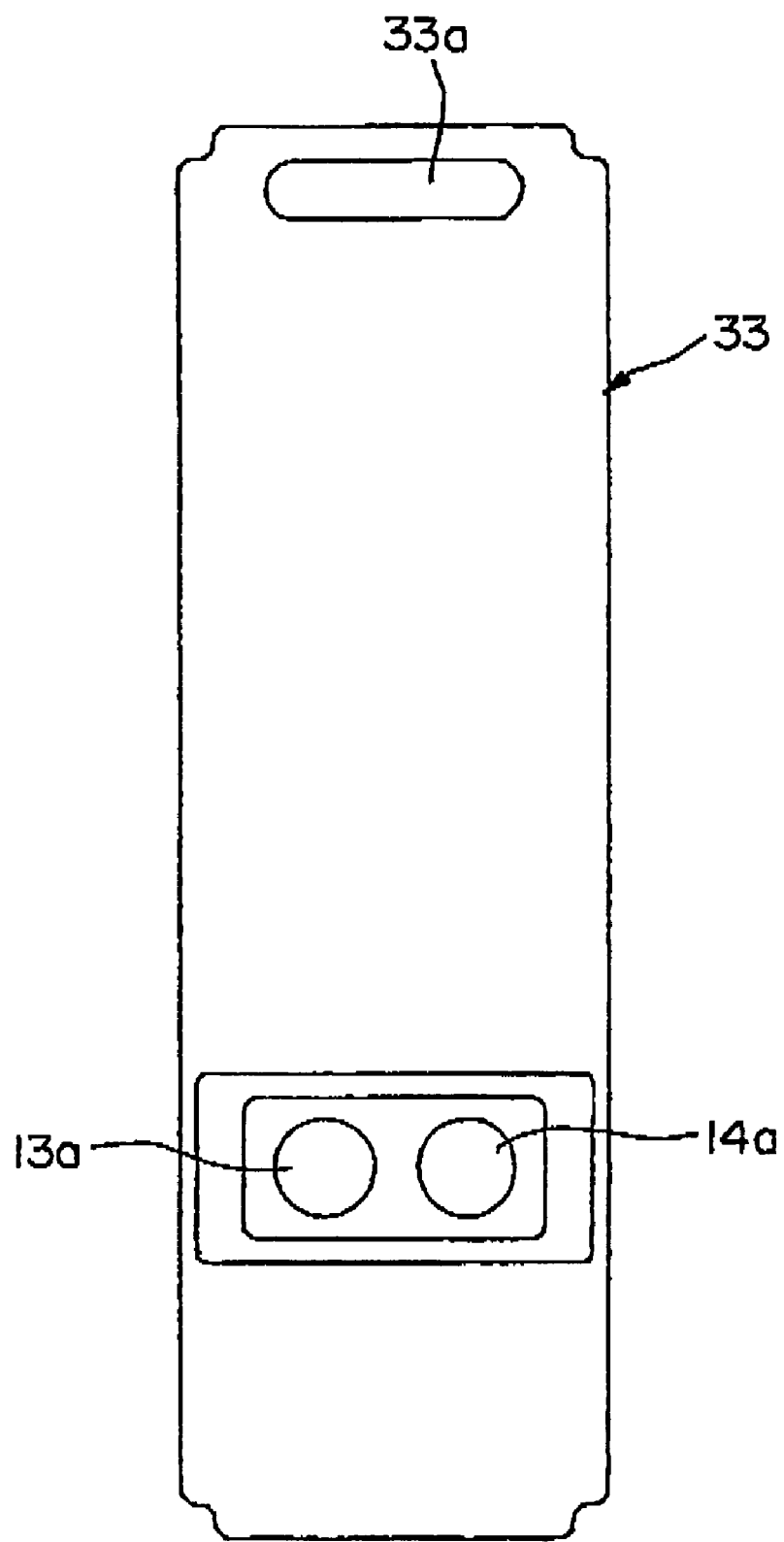
FIG. 6 is a plan view of a cover plate to be put on the surface of a device main body forming a sample measuring device.

These measuring chambers 13 and 14 are respectively equipped with transparent windows 13a and 14a for measurement (see FIG. 6). One window 13a is for measurement of the sample in one measuring chamber 13, and the other window 14a is for measurement of the sample in the other measuring chamber 14. Due to this arrangement, it is possible to measure absorbance, etc. of the sample in the measuring chambers 13 and 14 with different depths through the windows 13a and 14a.

There is provided an overflow chamber 27 on the centrifugal side of these two measuring chambers 13 and 14. The overflow chamber 27 allows entrance of the overflowing portion of the sample when the sample flows into the two measuring chambers 13 and 14, and accommodates the same; the overflow chamber 27 communicates with the measuring chambers 13 and 14 through a sixth back-flow preventing chamber 28.

Incidentally, as described above, the sample supply chamber 12, situated most upstream, communicates with the first back-flow preventing chamber 16 through the tubule 15, and the first back-flow preventing chamber 16 communicates with the first reagent melting/mixing means 11-1 through the passage 17; it is to be noted that the first back-flow preventing chamber 16 also communicates, through a tubule 31c, in series with a recovery chamber 31a arranged on the centrifugal side. The recovery chamber 31a serves to recover surplus sample remaining in the sample supply chamber 12 after flowing into the measuring chambers 13 and 14.

Embodiment 2

Figure 3:
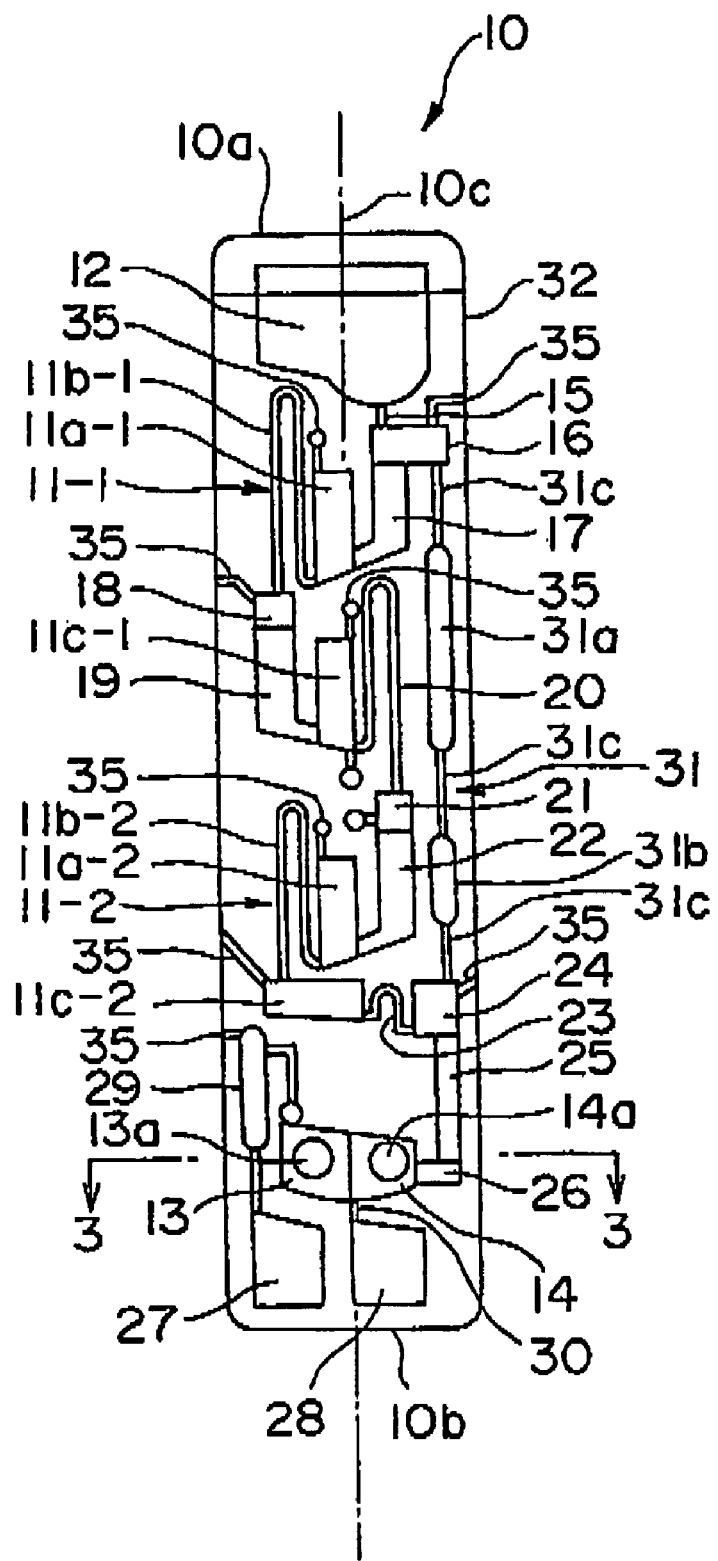
FIG. 3 is a plan view of a sample measuring device according to Embodiment 2.

In the example shown in FIG. 3, there is provided, on the centrifugal side of the measuring chambers 13 and 14, a disposal chamber 28 a part from the over flow chamber 27. The disposal chamber 28 serves to dispose of and recover the sample which has flowed into the measuring chambers 13 and 14 and undergone measurement; the disposal chamber 28 communicates with the measurement chambers 13 and 14 through a tubule 30.

Further, as shown in FIG. 3, in this example, there is formed a communication passage 31 further extending from the first back-flow preventing chamber 16 in the centrifugal direction and communicating with the fourth back-flow preventing chamber 24. As stated above, the fourth back-flow preventing chamber 24 communicates with the measuring chambers 13 and 14 through the passage 25 and the fifth back-flow preventing chamber 26, with the result that, due to the presence of this communication passage 31, the sample supply chamber 12 communicates with the measuring chambers 13 and 14, bypassing the first and second reagent melting/mixing means 11-1 and 11-2.

In this communication passage 31, the sixth back-flow preventing chamber 31a and the seventh back-flow preventing chamber 31b are arranged in series in the centrifugal direction, and communication is established between the sixth back-flow preventing chamber 31a and the seventh back-flow preventing chamber 31b and between the first back-flow preventing chamber 16 and the fourth back-flow preventing chamber 24, situated on the upstream and downstream sides of the communication passage 31, respectively through the tubules 31c and 31c.

What is important in this regard is as follows: imparting a centrifugal force, serving as an action force for causing the sample to flow from the sample supply chamber to the measuring chambers, to the sample measuring device 10 installed in the rotor of a centrifugal machine results in the sample flowing from the sample supply chamber 12 and through the first and second reagent melting/mixing means 11-1 and 11-2, and, in this process, the reagent is melted and flows into the measuring chambers 13 and 14; however, prior to this, a sample blank flows from the sample supply chamber 12 to the measuring chambers 13 and 14 through the bypass communication passage 31. In other words, it is necessary that the flow passages from the sample supply chamber 12 to the measuring chambers 13 and 14 be formed such that the time it takes the sample to flow from the sample supply chamber 12 into the measuring chambers 13 and 14 through the first and second reagent melting/mixing means 11-1 and 11-2 is longer than the time it takes the sample to flow directly into the measuring chambers 13 and 14 from the sample supply chamber 12 through the communication passage 31 (thus generating a time lag).

The sample measuring device 10 of Embodiments 1 and 2, described above, is composed of two components: the flat device main body 32 and the cover plate 33 put on the surface thereof. This structure will be described with reference to Embodiment 2 shown in FIG. 3.

A large number of recesses and grooves are formed in the surface of the device main body 32. These are provided so as to form the above-described elements of the device main body 32. That is, they are formed so as to define the sample supply chamber 12, the reagent melting chamber 11a-1 and the mixing chamber 11c-1 forming the first reagent melting/mixing means 11-1, the measuring chambers 13 and 14, the overflow chamber 27, the recovery chamber 29, the communication tubule 15 establishing communication between the sample supply chamber 12 and the first reagent melting/mixing means 11-1, the siphon tubule for establishing communication between the first and second reagent melting/mixing means 11-1 and 11-2 through the siphon 20, the siphon tubule for establishing communication between the reagent melting chamber 11a-1 and the mixing chamber 11c-1 through the siphon 11b-1, the siphon tubule for establishing communication between the second reagent melting chamber 11a-2 and the second mixing chamber 11c-2 through the third siphon 11b-2, the back-flow preventing chambers, etc., respectively at positions in conformity with what has been described above.

Then, the cover plate 33 shown in FIG. 5 is put on the surface of the flat device main body 32 to close the recesses and groove portions. In this process, as is apparent from FIG. 4, which is a sectional view, partly in section, of the sample measuring device 10 of this embodiment, on the surface of the device main body 32, there are previously formed, on the sides of the groove portions, ribs 34 of minute height, and, when the cover plate 33 is placed on the surface of the device main body 32, the inner side of the cover plate 33 is brought into press contact with the upper edges of the ribs 34, whereby it is possible to prevent leakage of the sample from the communication passages formed by the groove portions.

The positions where the ribs 34 are formed are not restricted to the sides of the groove portions; it is also possible to provide them around the recesses as needed, or form such a rib as a partition means separating from each other, the recesses forming the two measuring chambers 13 and 14.

In this way, the recesses and groove portions formed in the surface of the device main body 32 are substantially closed, with the result that these recesses and groove portions form the above-mentioned sample supply chamber 12, the reagent melting chamber 11a and the mixing chamber tic constituting the first reagent melting/fixing means 11-1, the second reagent melting chamber 11a-2 and the second mixing chamber 11c-2 constituting the second reagent melting/fixing means 11-2, the measuring chambers 13 and 14, the overflow chamber 27, the recovery chamber 29, and the first through seventh back-flow preventing chambers 16, 18, 21, 24, 26, 31a, and 31b.

The first through seventh back-flow preventing chambers 16, 18, 21, 24, 26, 31a, and 31b are formed in order to avoid unnecessary movement of the sample. More specifically, the recesses constituting the recesses forming the back-flow preventing chambers are formed deeper than the communication passages communicating with the recesses forming the sample supply chamber 12, the reagent melting chamber 11a and the mixing chamber 11c constituting the first reagent melting/fixing means 11-1, the second reagent melting chamber 11a-2 and the second mixing chamber 11c-2 constituting the second reagent melting/fixing means 11-2, the measuring chamber 13, and the overflow chamber 27, or the recovery chamber 29.

Further, the groove portions forming the passages 17, 19, 22, and 25, the siphon tubules of the first through third siphons 11b, 20, and 23, and the tubules 15 and 31c are formed shallower than the recesses forming the sample supply chamber 12, the reagent melting chamber 11a-1 and the mixing chamber 11c-1 constituting the first reagent melting/fixing means 11-1, the second reagent melting chamber 11a-2 and the second mixing chamber 11c-2 constituting the second reagent melting/fixing means 11-2, the measuring chambers 13 and 14, the overflow chamber 27, and the disposal chamber 28. It is desirable that the depth of the groove portions constituting these passages, siphons, and tubules be approximately 0.01 to 1.5 mm.

In other words, the recesses forming the sample supply chamber 12, the reagent melting chamber 11a-1 and the mixing chamber 11c-1 constituting the first reagent melting/fixing means 11-1, the second reagent melting chamber 11a-2 and the second mixing chamber 11c-2 constituting the second reagent melting/fixing means 11-2, the measuring chambers 13 and 14, the overflow chamber 27, and the disposal chamber 28 are deeper than the groove portions forming the passages, siphon tubules, etc.; further, the recesses forming the-first through seventh back-flow preventing chambers 16, 18, 21, 24, 26, 31a, and 31b are formed deeper than the sample supply chamber 12, the sample melting chamber 11a, etc.

As shown in FIG. 6, the cover plate 33 has a supply port 33a for supplying the sample to the sample supply chamber 12 at the portion thereof closing the recess forming the sample supply chamber 12 when the cover plate is put on the surface of the device main body 32.

Further, the windows 13a and 14a of the measuring chambers 13 and 14 are provided at the portions thereof closing the recesses forming the measuring chambers 13 and 14 when the cover plate 33 is put on the surface of the device main body 32.

As the material of the flat device main body 32 and the cover plate 33, transparent resins, such as PMMA, polystyrene, and polycarbonate are suitable; from the viewpoint of light transmittance, PMMA is the most suitable. The device main body 32 and the cover plate 33 are firmly attached to each other by ultrasonic welding, double-sided adhesive tape, adhesive, solvent, or the like. From the viewpoint of productivity and liquid leakage prevention, ultrasonic welding is the most suitable as the means for bonding the device main body 32 and the cover plate 33 to each other.

Figure 7:
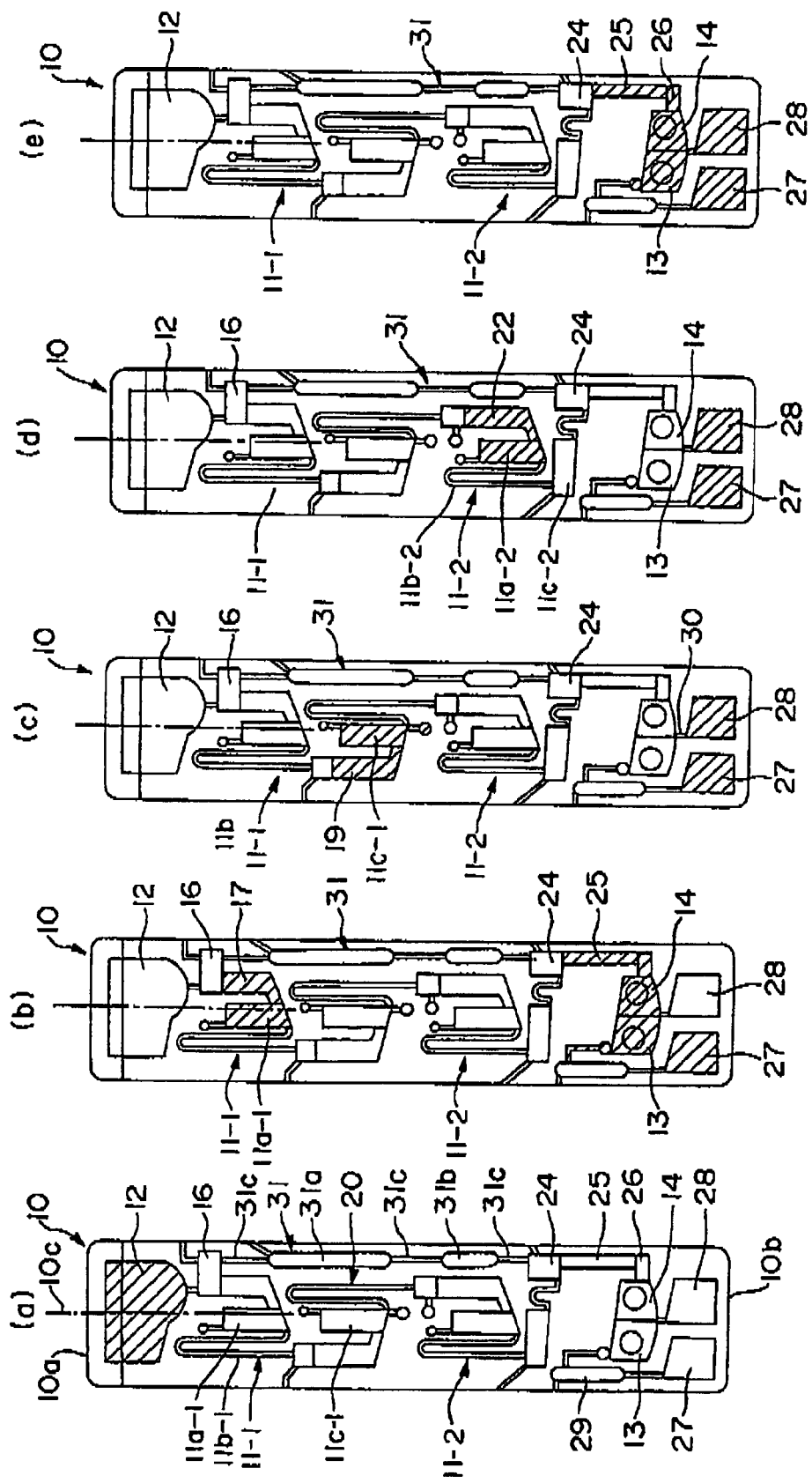
FIGS. 7($a$) through 7($e$) are plan views of a sample measuring device, showing how a specimen constituting a sample eventually reaches an overflow chamber from a sample supply chamber of a sample measuring device when the rotor of a centrifugal machine is repeatedly rotated and stopped, with the sample measuring device being on the rotor of the centrifugal machine.

Next, the way the sample measuring device 10 is used will be described with reference to FIG. 7 while adding some structural description. In FIG. 7, the shaded areas are the portions where the sample flows in (the chambers, siphons, tubules, etc. described above). When the sample to be measured is blood plasma, blood is previously separated into blood plasma and blood corpuscles by a process and device (not shown), and this blood plasma is diluted by a diluent and retained in a dispenser (indicated by reference numeral 40 in FIG. 5).

First, as shown in FIG. 5, the sample (diluted blood plasma) is supplied from the dispenser 40 to the sample supply chamber 12 through the supply port 34 provided on the cover plate 33. At this time, the sample has only to be supplied in a relatively large amount, and does not require accurate determination. When the sample has been dispensed to the sample supply chamber 12 as shown in FIG. 7(a), the first centrifugal operation is conducted.

Through this centrifugal operation, the sample in the sample supply chamber 12 flows into the first back-flow preventing chamber 16 through the tubule 15, and flows into the reagent melting chamber 11a-1 of the first reagent melting/mixing means 11-1 through the passage 17 as shown in FIG. 7(b). The portion of the sample which has not been able to enter the sample melting chamber 11a-1, that is, the surplus sample in the sample supply chamber 12, is sent from the first back-flow preventing chamber 16 through the tubule 30 to the recovery chamber 29 for recovery.

A dried reagent is contained in the reagent melting chamber 11a-1 of the first reagent melting/mixing means 11-1. This dried reagent consists of a reagent applied to a film and dried thereon, the film being previously put into the reagent melting chamber 11a-1. In this invention, the reagent is naturally not limited to a dried reagent applied to a film; it is also possible to use various types of reagent, such as a tablet-like reagent, a freeze-dried reagent, or a powdered reagent.

When the rotor R rotates one or a predetermined times and the sample flows from the sample supply chamber 12 into the reagent melting chamber 11a-1 of the first reagent melting/mixing means 11-1, the dried reagent applied to the film is dissolved in the sample. As can be seen from the above illustration, the sample melting chamber 11a-1 serves at once as the retaining chamber for retaining the reagent to be dissolved in the sample and as the measuring means for measuring the quantity of the specimen.

As a result, this sample measuring device 10 is inexpensive and superior in function.

The sample with the dried reagent dissolved therein fills the siphon tubule constituting the siphon 11c-1 by capillary action while the rotor R is at rest, whereby the sample is made ready to flow into the next chamber, that is, the mixing chamber 11b-1. Thereafter, the rotor R is rotated (for the second time), whereby the reagent and sample in the reagent melting chamber 11a-1 moves by siphon phenomenon while being mixed together as shown in FIG. 7(c) to flow into the mixing chamber 11b-l, where the sample and reagent are uniformly mixed together and, at the same time, the requisite reaction for measurement takes place.

The reagent and sample, having been uniformly mixed together and undergone the requisite reaction for measurement in the mixing chamber 11b-l, fills the siphon tubule constituting the second siphon 20 by capillary action while the rotor R is at rest, whereby the sample is made ready to flow into the second reagent melting chamber 11a-2 of the second reagent melting/mixing means 11-2. Thereafter, the rotor R is rotated (for the third time), whereby reagent-reacted sample in the second mixing chamber 11c-2 moves by siphon phenomenon to flow into the second reagent melting chamber 11a-2.

In this way, the sample successively moves from the sample supply chamber 12 to the first reagent melting/mixing means 11-1 and then to the second reagent melting/mixing means 11-2, and predetermined reagents are dissolved in the sample in the respective reagent melting chambers 11a-1 and 11a-2; further, the reagent dissolved in the sample are uniformly mixed in the respective mixing chambers 11c-1 and 11c-2. Thereafter, as shown in FIG. 7(e), the sample with the reagents dissolved therein eventually flows into the two measuring chambers 13 and 14 for the requisite measurement of absorbance, etc.

If, in the reagent melting/mixing means, solely the melting of the reagent is required, the mixing chambers 11c-1 and 11c-2 may be omitted as appropriate. That is, the mixing chambers are not necessary when there is no need to effect uniform mixing and reaction at each stage as in the case, for example, in which reagents subject to deterioration if stored together are just separated from each other for stable storage. However, it goes without saying that the mixing chambers are necessary if uniform mixing and reaction are to be effected at each stage.

In the above-described manner in which the sample measuring device 10 is used, in order that the sample may flow smoothly from the sample supply chamber 12 to the measuring chamber 13, air vent holes are provided at appropriate positions. These air vent holes do not require their formation at specific positions; they can be formed at appropriate positions by experimentally ascertaining the way the reagent or the sample with the reagent dissolved therein flows.

In the sample measuring device 10 of this embodiment, the air vent holes are indicated by reference numeral 35 in FIGS. 1 and 3; to mention the positions where they are formed, from the upstream side, they are: the first through fourth back-flow preventing chambers 16, 18, 21, and 24, the reagent melting chamber 11a-1 and the mixing chamber 11c-1 of the first reagent melting/mixing means 11-1, and the second reagent melting chamber 11a-2 and the second mixing chamber 11c-2 of the second reagent melting/mixing means 11-2.

In this way, in the sample measuring device 10 of this embodiment, the first and second reagent melting/mixing means 11-1 and 11-2 are provided so as to allow them to communicate with each other in series, whereby it is possible to repeatedly effect the melting and mixing of two reagents.

As described above, in the sample measuring device of the present invention, a plurality of reagent melting/mixing means are provided so as to allow them to communicate with each other in series, whereby it is possible to repeatedly effect the melting and mixing of a plurality of reagents, making it possible to cope with a case in which multi-reagent reactions are to be effected.

While in the sample measuring device 10 of the above-described embodiment the sample with the reagent dissolved therein fills the siphon tubule constituting the siphon 11c-1 (11c-2) by capillary action while the rotor R is at rest, and the sample having flowed into the two measuring chambers 13 and 14 is measured for absorbance, etc. while the rotor R is at rest, the present invention is not restricted to this operation. For example, it is also possible to generate siphon phenomenon by not completely stopping the rotation of the rotor and reducing the RPM thereof; further, it is also possible to perform measurement without stopping the rotation of the rotor.

By thus generating siphon phenomenon without stopping the rotation of the rotor while reducing the RPM thereof, or performing measurement without stopping the rotation of the rotor, it is possible to make the effect of each back-flow preventing chamber still more perfect; in some cases, it is possible to suppress generation of back flow without providing any back-flow preventing chamber.

Further, while in the above-described example, the sample measuring device 10 is used to measure the absorbance of the sample flowing into the measuring chambers, the present invention is not restricted to absorbance measurement; it can also be used to measure the properties of a sample by various optical measurement means including measurement through reflection light, or perform measurement on a sample in the measuring chamber by an electro-chemical measurement means, or to measure the properties of a sample in the measuring chamber by utilizing any well-known measurement means. Thus, the measuring chamber provided in the sample measuring device of the present invention should be constructed in conformity with such various measurement means; for example, it is not always necessary for the windows to be transparent or for the measuring chamber to consist of two or more chambers with different depths.

Thereafter, the rotor R is rotated (for the second time), whereby the sample with the reagent in the reagent melting chamber 11a-1 moves by siphon phenomenon while being mixed together and flows into the mixing chamber 11c-1 (11c-2), where the sample and the reagent are uniformly mixed together, and the requisite reaction for measurement takes place. At the same time, the sample blank having flowed into the measuring chambers 13 and 14 and undergone photometric analysis moves to the disposal chamber 28, thus emptying the measuring chambers 13 and 14.

Embodiment 3

Figure 8:
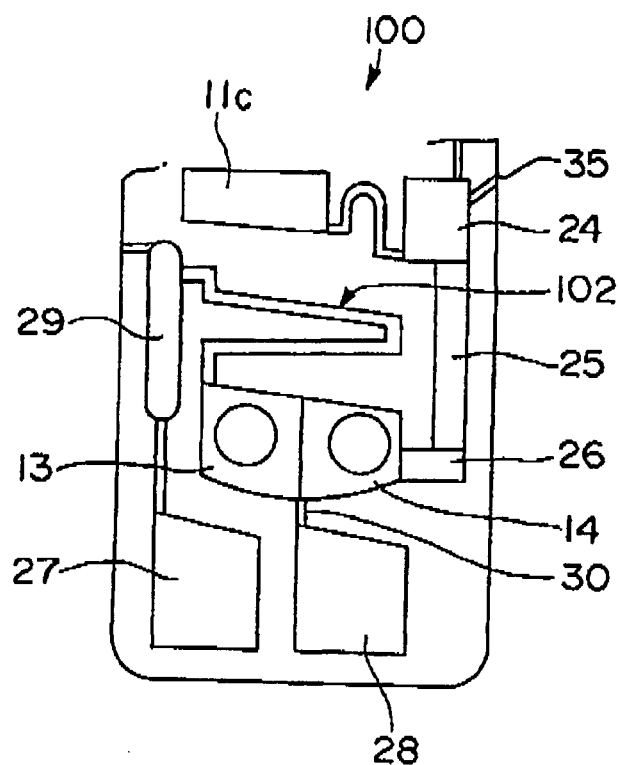
FIG. 8 is a plan view partially showing a main portion of a sample measuring device according to Embodiment 3.

FIG. 8 shows a main portion of a sample measuring device according to another embodiment of the present invention. In FIG. 8, the components that are the same as or equivalent to those of the sample measuring device 10 shown in FIG. 3 are indicated by the same reference numerals, and a detailed description of such components will be omitted.

The construction of the sample measuring device 100 of the embodiment shown in FIG. 8 differs from that of the sample measuring device 10 shown in FIG. 3 in that, in the flow passage from the measuring chambers 13 and 14 to the overflow chamber 27, there is used a tubule 102 whose total length is increased through a lateral U-shaped configuration as a communication means between the measuring chambers 13 and 14 and the back-flow preventing chamber 29.

In general, when the length of the tubule 102 is small, back flow or drying of the liquid may occur when measurement is performed with the rotor being at rest or reduced in rotating speed, allowing bubbles to enter the measuring portion; in this embodiment, however, by establishing communication between the measuring chambers 13 and 14 and the back-flow preventing chamber 29 through the tubule 102 whose length is increased due to the lateral U-shaped configuration, bubbles are not easily allowed to enter the measuring portion, making it possible to perform accurate measurement.

Embodiment 4

Figure 9:
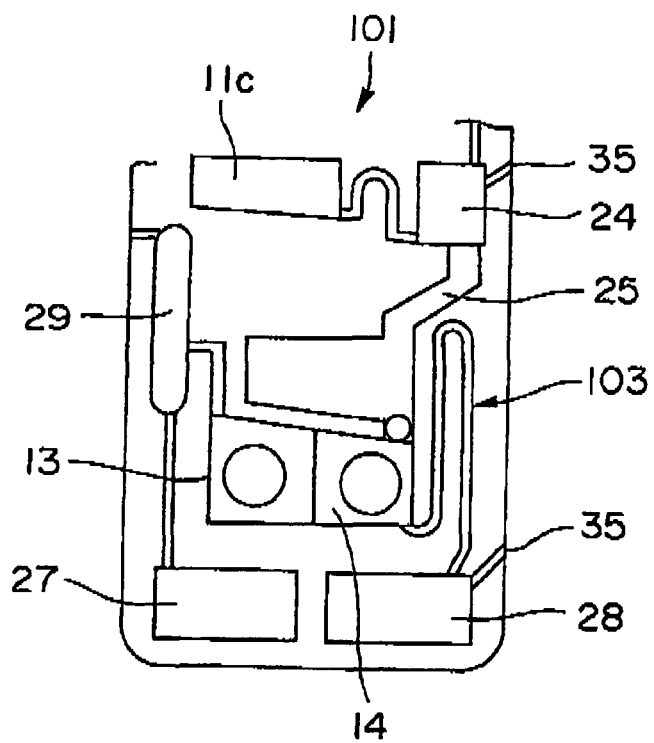
FIG. 9 is a plan view partially showing a main portion of a sample measuring device according to Embodiment 4.

FIG. 9 shows a main portion of a sample measuring device according to still another embodiment of the present invention. In FIG. 9, the components that are the same as or equivalent to those of the sample measuring device 10 shown in FIG.

3 are indicated by the same reference numerals, and a detailed description of such components will be omitted. The construction of this sample measuring device 101 differs from that of the sample measuring device 10 shown in FIG. 3 in that there is adopted another communication structure for moving the sample blank that has undergone measurement in the measuring chambers 13 and 14 to the disposal chamber 29. As described above, in the case of the sample measuring device 10 of the embodiment shown in FIG. 3, the measuring chambers 13 and 14 and the disposal chamber 28 communicate with each other through the tubule 30.

Incidentally, when, in the case of the sample measuring device 10 of the embodiment shown in FIG. 3, the sample blank is to be moved from the sample supply chamber 12 to the measuring chambers 13 and 14 through the communication passage 31, a small centrifugal force of approximately 100 G is applied, whereas, when the sample blank in the measuring chambers 13 and 14 is to be put in the disposal chamber 28, a large centrifugal force of approximately 300 G is applied.

That is, the movement of the sample blank is controlled by the magnitude of the centrifugal force. In this case, when the inlet for the sample blank to the measuring chambers 13 and 14 is provided on the side farther from the centrifugal center, there is no fear of the sample blank erroneously entering the disposal chamber 28, so that it is possible to ensure operational reliability. It is to be noted that in the case of this construction, no air vent hole is provided in the disposal chamber 28.

In contrast, in the case of the sample measuring device 101 of this embodiment shown in FIG. 9, the communication passage from the measuring chambers 13 and 14 to the disposal chamber 28 is formed by a fourth siphon 103. In this case, the sample blank put in the measuring chambers 13 and 14 fills the siphon tubule forming the fourth siphon 103 by capillary action during photometric analysis with the rotor R being at rest, whereby the sample blank is made ready to flow into the disposal chamber 28.

When the rotor R subsequently rotates, the sample blank in the measuring chambers 13 and 14 flows into the disposal chamber 28. That is, in this case, it is possible to cause the sample blank to flow into the disposal chamber in synchronism with the movement of the sample and the reagent-reaction sample. It is to be noted that, in the case of the sample measuring device 101 of the embodiment shown in FIG. 9, it is desirable that an air vent hole 35 be formed in the disposal chamber 28.

While the first through fourth embodiments have been described with reference to the case in which the first and second reagent melting/mixing means are caused to communicated with each other in series, this should not be construed restrictively; if, on the above principle, three or more reagent melting/mixing means are provided so as to be capable of communicating with each other in series, it is possible to repeatedly effect the melting and mixing of a plurality of reagents, thereby making it possible to cope with multi-reagent type reaction.

Embodiment 5

Figure 10:
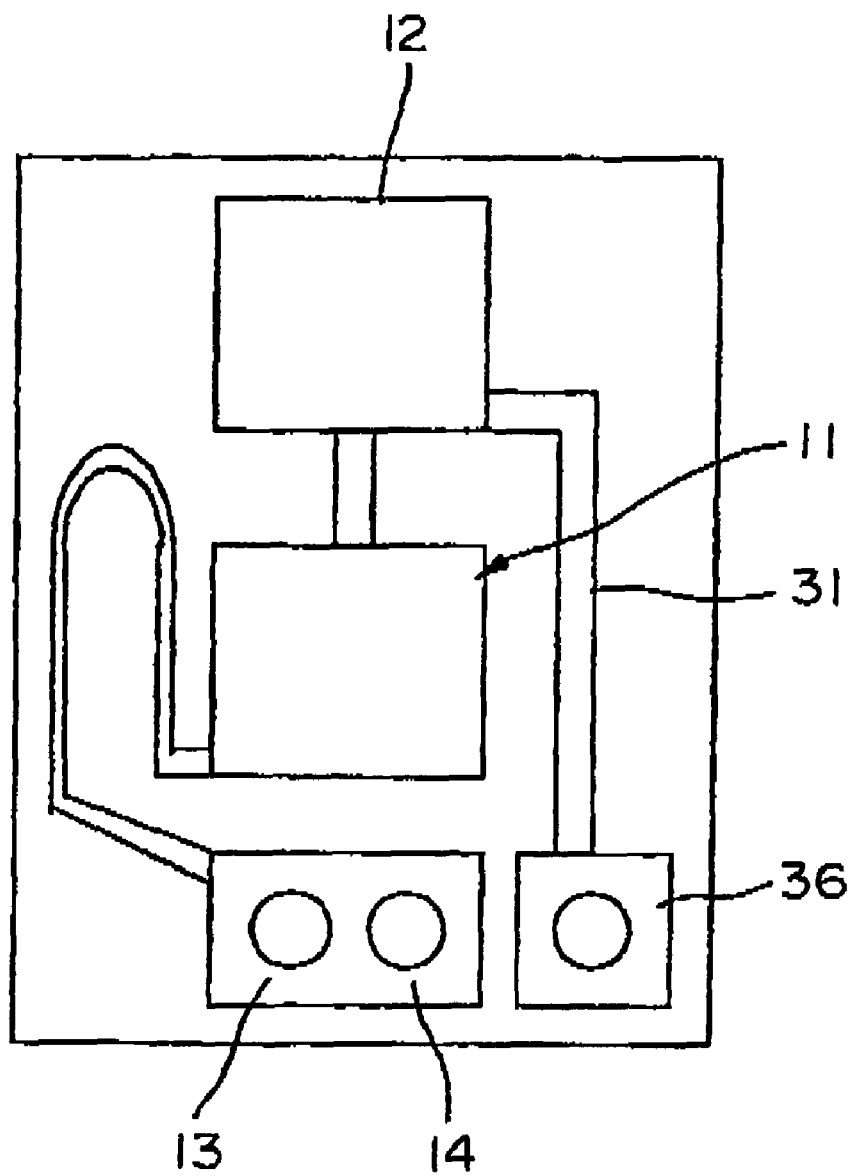
FIG. 10 is an explanatory constructional view diagrammatically and schematically showing a main portion of a sample measuring device according to Embodiment 5.

Further, while in the sample measuring device of Embodiment 9 described above the measurement of the sample blank and the measurement of the reagent-reaction sample are performed in the same measuring chamber, it is also possible, as shown diagrammatically and schematically in FIG. 10, to provide a plurality of measuring chambers 13, 14, and 36, and to use at least one measuring chamber 36 among them as a chamber dedicated to sample blank measurement, causing one or a plurality of reagent melting/mixing means 11 to communicate with the sample supply chamber 12 through bypassing, and causing the other measuring chambers 13 and 14 to communicate with the sample supply chamber 12 through one or a plurality of reagent melting/mixing means.

Embodiment 6

This embodiment differs from the above-described Embodiments 1 through 5 in that it employs a pressure generating means for moving the sample in the flow passage.

As described above, in the sample measuring device of the present invention, communication is established between the sample supply chamber, the reagent melting/mixing means, the measuring chamber, etc., so that the sample moves from the sample supply chamber by way of the reagent melting/mixing means to reach the measuring chamber on the most downstream side. By utilizing suction or pressurization due to a pump means constituting the pressure generating means, the sample is moved in a predetermined flow passage from the reagent supply chamber on the upstream side to the measuring chamber on the downstream side.

In the following, this embodiment will be described in detail with reference to FIGS. 11 through 16.

Figure 11:
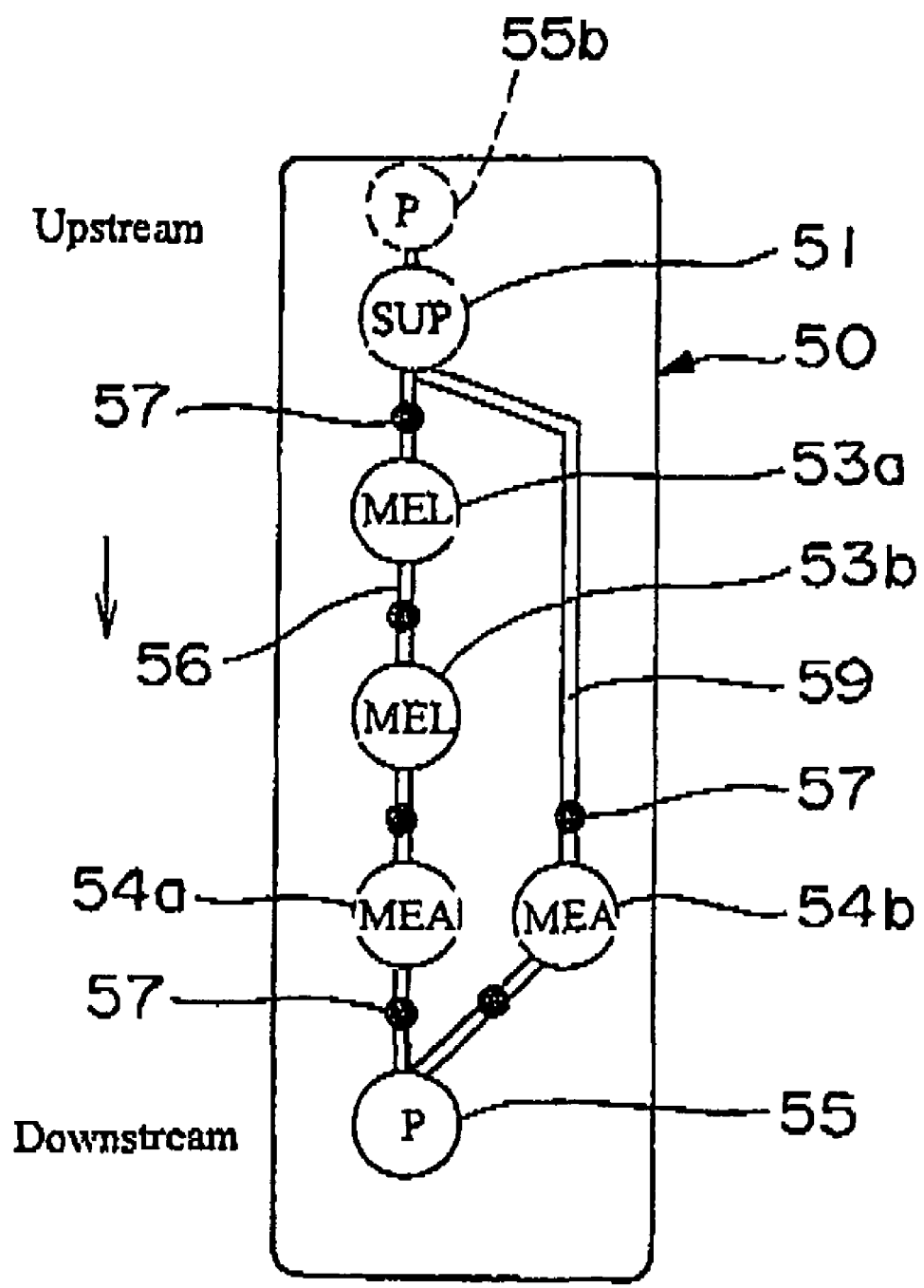
FIG. 11 is a plan view showing a sample measuring device according to Embodiment 6.

FIG. 11 shows a device main body 50 in which there are arranged, in series from the upstream side, a reagent supply chamber 51, a first reagent melting/mixing means 53a, a second reagent melting/mixing means 53b, and a measuring chamber 54a, with communication being established between these components through a flow passage 56. In this example, a suction pump 55 is provided on the downstream side, and this pump 55 is connected to an end of the flow passage 56 on the downstream side of the measuring chamber 54a, the reagent in the flow passage 56 being moved from the reagent supply chamber 51 toward the measuring chamber 54a through suction by this pump 55. Further, liquid flow control means 57 are provided between the reagent supply chamber 51 and the first reagent melting/mixing means 53a, between the first reagent melting/mixing means 53a and the second reagent melting/mixing means 53b, between the second reagent melting/mixing means 53b and the measuring chamber 54a, between the measuring chamber 54a and the pump 55, etc. These liquid flow control means 57 perform liquid flow control in place of the siphons in the above-described embodiments.

On the other hand, there is formed a bypass passage 59 branching off from the downstream side of the reagent supply chamber 51 to communicate with the second measuring chamber 54b, reaching the pump 55 from the second measuring chamber 54b. This bypass passage 59 is mainly used for specimen blank measurement.

Embodiment 7

Figure 12:
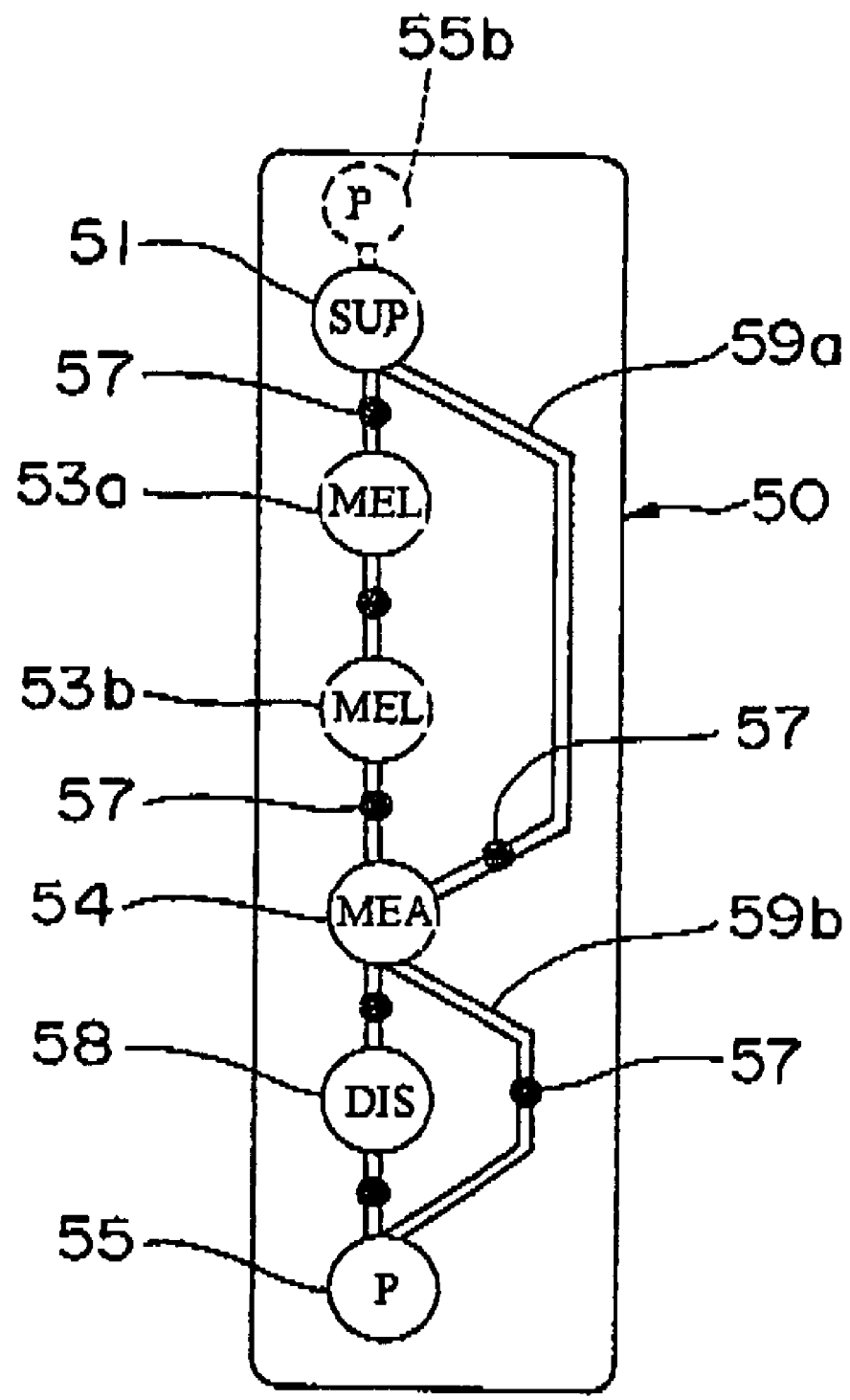
FIG. 12 is a plan view showing a sample measuring device according to Embodiment 7.

FIG. 12 shows another embodiment of the present information, in which a disposal chamber 58 is provided on the downstream side of the measuring chamber 54. Further, there are formed two bypass passages. One bypass passage 59 allows the reagent supply chamber 51 to communicate with the measuring chamber 54 without passing the first reagent melting/mixing means 53a and the second reagent melting/mixing means 53b. The other, second bypass passage 59b leads from the measuring chamber 54 to the pump 55 without passing the disposal chamber 58.

While in Embodiments 6 and 7 described above the pump 55 is provided at the most downstream end of the flow passage

56, it is also possible to provide a pump 55b at the most upstream end of the flow passage 56, as indicated by the dashed line in FIGS. 11 and 12. In this case, the upstream side pump 55b functions as a pressurizing pump which pressurizes the interior of the passage 56 to move the sample. Further, it is possible to provide the pump 55b together with the downstream pump 55a or to provide it alone without providing the downstream pump 55a.

Further, while in Embodiments 6 and 7 described above the pump 55a, 55b is provided on the sample measuring device, it is also possible to provide no such pump on the sample measuring device but connect an external pump (not shown) to an end of the flow passage 56. In this case, when the pump is to be installed on the downstream side of the measuring device, a suction pump is connected to the lower end of the flow passage. On the other hand, when the pump means is to be installed on the upstream side of the measuring device, a pressurizing pump is connected to the upper end of the flow passage.

In the following, the liquid flow control means and the pump means shown in Embodiments 6 and 7 will be described in detail.

Figure 13:
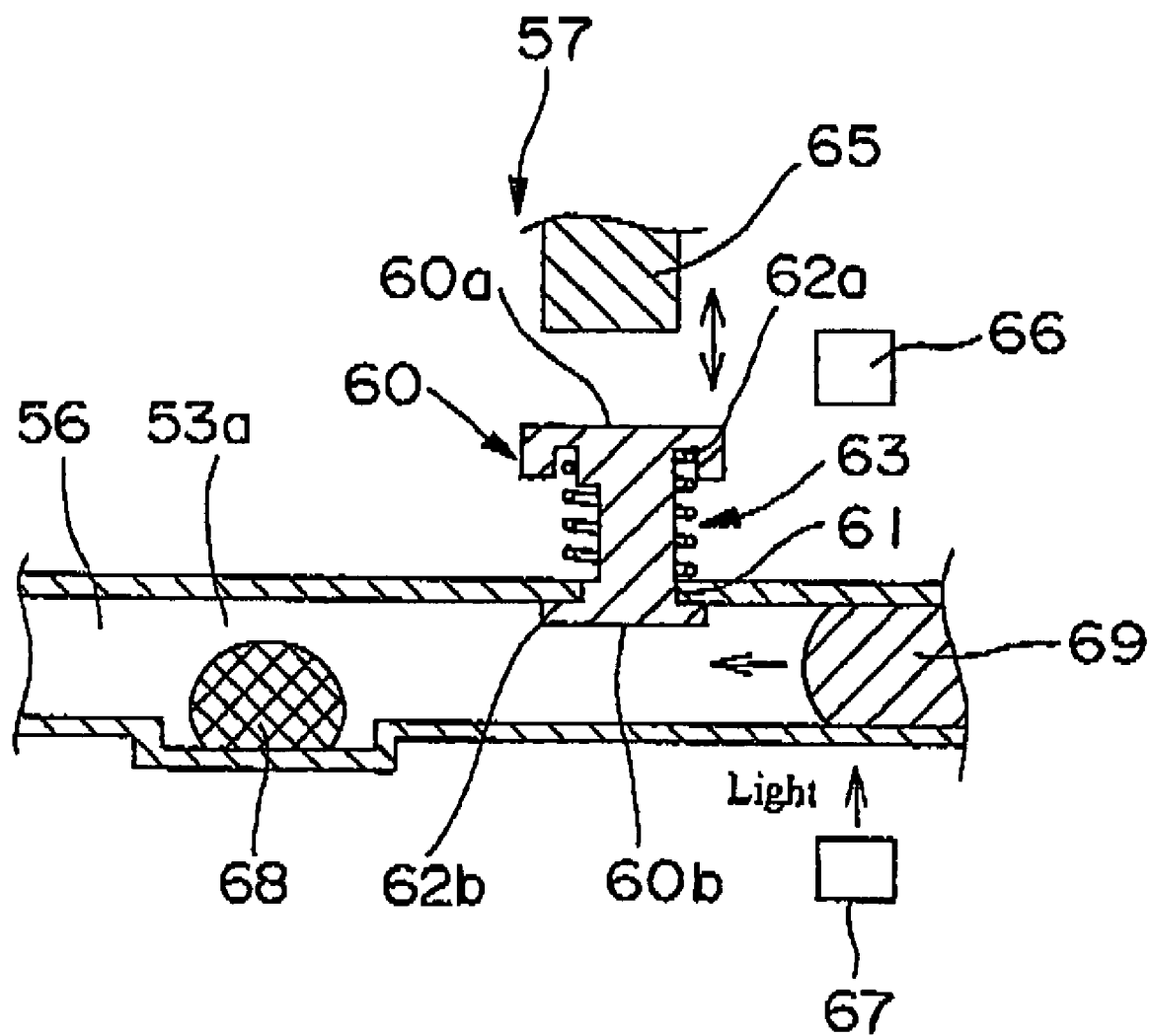
FIG. 13 is a diagram showing in detail a liquid flow control means.

The liquid flow control means 57 has a structure as shown in FIG. 13, in which, in the portion of the flow passage 56 in the vicinity of the reagent melting/mixing means 53a with a reagent 68 arranged therein, there is provided a valve body 60 capable of opening and closing the flow passage 56. This valve body 60 is formed of a deformable material, such as rubber or synthetic resin, and has, in the direction perpendicular to the liquid flowing direction, a flow passage cut-off surface with a configuration and size substantially in conformity with the sectional configuration of the flow passage 60, which is, for example, circular. This valve body 60 has its lower end portion 60b inserted into a through-hole 61 provided in a part of the outer periphery of the tube constituting the flow passage 60, thus closing the through-hole 61. The valve body 60 is regulated in its movable range by flange-like stoppers 62a and 62b provided at the upper and lower ends thereof, wherein the stopper 62b at the lower end is larger than the through-hole 61, so that the valve body is kept from being detached from the tube constituting the flow passage 56. Further, this valve body 60 is constantly urged so as to be opened by a spring 63 provided between the outer periphery of the flow passage 56 and the stoppers 62a and 62b at the upper and lower ends of the valve body 60.

This spring 63 may be of any type as long as it retains the valve body 60 while urging it in the opening direction.

On the other hand, there is provided on the outer side a pressurizing member 65 for pressurizing the upper end 60a of the valve body 60 to push down the valve body 60 against the urging force of the spring 63 to thereby keep it closed.

In the above-described liquid flow control means 57, the flow passage 56 can be opened and closed by changing the position of the valve body 60 through pressurization/non-pressurization by the pressurizing member 65. Further, the valve body 60 is provided with an air vent hole for bleeding air, thereby making it possible to smoothen the liquid flow in the flow passage 56.

Further, as shown in FIG. 13, as a means for detecting the liquid flow 69, an optical sensor 67 is installed in the periphery of the flow passage 56. The optical sensor 67 is equipped with a light receiving portion 66 installed on the opposite side with respect to the flow passage 56. The light receiving portion 66 receives light emitted from the optical sensor 67 and passed through the flow passage 56, whereby it is possible to detect the presence of any sample flowing through the flow passage 56. Since light is transmitted through the flow passage 56 to detect liquid from a change in transmissivity, it is advantageous in detecting minute changes in a flow of a minute amount of sample.

Examples of other sensors that can be employed here include a sensor which detects changes in conduction when it comes into contact with liquid by using an electrode, a sensor which detect the presence of liquid by emitting ultrasonic waves, and a sensor which detects changes in electrostatic capacitance in the presence/absence of liquid.

Figure 14:
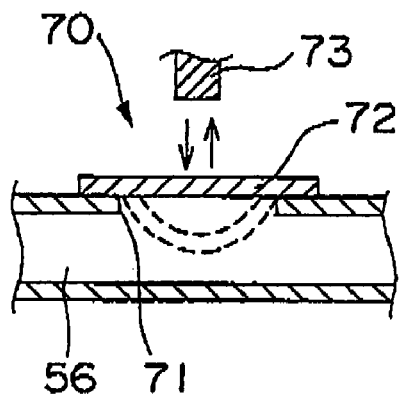
FIG. 14 is a diagram showing an example of a pump.
Figure 15:
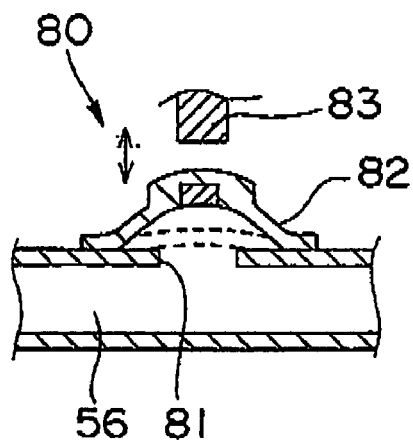
FIG. 15 is a diagram showing another example of the pump.
Figure 16:
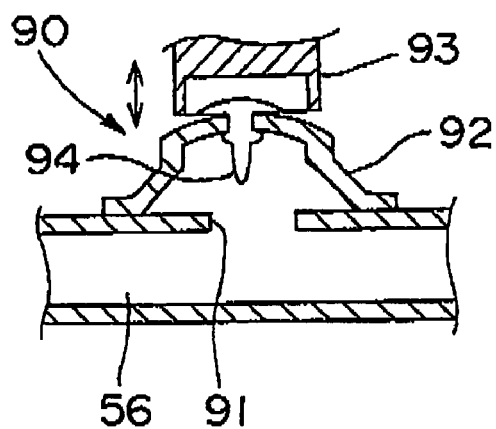
FIG. 16 is a diagram showing still another example of the pump.

Next, the construction of the pump 55a, 55b will be described. The pump 55 is of the type provided on the measuring device; FIGS. 14 through 16 show different examples of the pump structure.

A pump 70 shown in FIG. 14 is equipped with a hole portion 71 provided in the outer periphery of the tubular flow passage 56 and a deformable film 72 bonded to the periphery of the hole portion 71 to cover the same. This film 72 is pressurized from outside toward the interior of the flow passage 56 by a pressurizing member 73 provided in the exterior. When the film 72 is deformed so as to be curved toward the interior of the flow passage 56 as indicated by the dashed lines, the pressure inside the flow passage 56 increases. Further, when the film 72 is pressurized first and then released to restore the film 72 to the original state, the pressure in the flow passage 56 can be reduced, which means this pump 70 can also be used as a suction pump.

A pump 80 shown in FIG. 15 is equipped with a hole portion 81 provided in the outer periphery of the tubular flow passage 56 and a plate-like convex member 82 bonded to the periphery of the hole portion 81 to cover the same. This convex member 82 consists of an elastic member; when it is pressurized by a pressurizing member 83 provided in the exterior and is deformed inwardly so as to become flat as indicated by the dashed lines, the pressure in the flow passages 56 increases. Conversely, when the convex member 82 is first pressurized and maintained in the flat state, and then released, the convex member 82 is restored to the original state as indicated by the solid lines, and is separated from the hole portion 81, whereby the pressure in the flow passage 56 is reduced.

The pump 90 shown in FIG. 16 has a similar construction and effect as that shown in FIG. 15; when a convex member 92 is pressurized by a pressurizing member 93 provided in the exterior, the pressure in the flow passage 56 increases. Conversely, when the convex member 92 is first pressurized and maintained in the flat state, and then released, the convex member 92 is restored to the original state, and is separated from the hole portion 91, whereby the pressure in the flow passage 56 is reduced. In this pump 90, a check valve 94 is provided at the apex of the interior of the convex member 92. When the convex member 92 is pressurized by the pressurizing member 93 to be deformed into a flat shape, the check valve 94 is inserted into the flow passage 56, making it possible to close the same. Due to this arrangement, in addition to the increase and decrease in pressure inside the flow passage 56, it is possible to repeat the pressurizing operation any number of times even if there exists in the flow passage 56 a liquid constituting the sample.

A pump means as described above is installed in the flow passage 56 as needed as shown in the drawings; however, when the sample measuring device is formed solely by the flow passage 56 for melting/mixing reagent, it is not always necessary to provide the valve body 60 as described above. In such cases, the liquid flow can be controlled solely by the above-described detecting means, that is, the sensor for detecting the presence of the liquid flow. That is, when there is no need to cause liquid to flow through a bypass passage and only one flow route is provided, the expected results can be achieved by controlling the requisite time for the liquid flow, etc. through detection of the position of the liquid flow by the detecting means and adjustment of the pump pressure.

While the above-described pump is provided on the sample measuring device, it is also possible for the pump to be installed outside the sample measuring device and connected to an end of the flow passage 56. For example, it is possible to connect a syringe pump using a syringe (injection cylinder) to the opening of flow passage 56 at the lowermost end of the sample measuring device 50.

In the sample measuring device 50, constructed as described above, it is possible to move a sample, such as blood plasma, supplied to the sample supply chamber 51 successively downstream by the pressurization or suction force of the pump 55 or 55b. In this process, the sample flow is controlled to an appropriate state by the liquid flow control means 57. For example, back flow of the liquid is prevented, and the speed, flow time, etc. of the liquid are controlled. The sample flow from the sample supply chamber 51 into the first sample melting/mixing means 53a to be melted therein, and, further, the sample flows into the second sample melting/mixing means 53b, whereby the respective reagents are dissolved in the sample and mixed therewith. Finally, the sample with the reagents dissolved therein flows into the measuring chamber 54 (54a, 54b) for requisite measurement of absorbance, etc.

It is to be noted that, in the example shown in FIG. 12, it is possible to measure the sample blank and the sample with the reagent dissolved therein in the same measuring chamber with a time lag. The disposal chamber 58 is provided so that the sample after the measurement of the sample blank may flow into it.

In the sample measuring devices of Embodiments 6 and 7, the sample can be moved in the flow passage of the device main body by means of pressure, without using any centrifugal force. Thus, it is possible to execute sample measurement without using any centrifugal force generating device.

Industrial Applicability

The sample measuring device of the present invention can be used in the component analysis of a liquid, such as body liquid. This sample measuring device is easy to handle and allows the sample and reagent to be reliably mixed and agitated prior to photometric analysis, thereby achieving an improvement in accuracy and reliability in photometric analysis.

The invention claimed is:

1. A sample measuring device comprising:
    at least one reagent melting/mixing means;
    a sample supply chamber communicating with the reagent melting/mixing means to cause a sample to flow into the reagent melting/mixing means; and
    at least one measuring chamber communicating with the reagent melting/mixing means,
    wherein the sample supply chamber, the reagent melting/mixing means, and the measuring chamber are arranged from an upstream to a downstream side of a flow passage for a sample, which is moved by a sample moving means, and that the sample supply chamber is arranged on an upstream side of the reagent melting/mixing means, and the measuring chamber is arranged on a downstream side of the reagent melting/mixing means, and
    wherein the reagent melting/mixing means comprises a reagent melting chamber accommodating a reagent that is to react with the sample and a mixing chamber communicating with the reagent melting chamber through a siphon,
    a bypass passage, connecting the sample supply chamber and the measuring chamber, bypassing at least one of the following components provided between the sample supply chamber and the measuring chamber: the reagent melting chamber, the mixing chamber, and the reagent melting/mixing means including the reagent melting chamber and the mixing chamber, and
    wherein, when an action force causing the sample to flow from the sample supply chamber to the measuring chamber is imparted to the sample measuring device, there is generated a time lag in sample inflow into the measuring chamber such that, as compared with the flow passage which allows the sample from the sample supply chamber to reach the measuring chamber through the reagent melting/mixing means, the flow passage which allows the sample to reach the measuring chamber through the bypass passage causes the sample to flow into the measuring chamber through the bypass passage before the sample from the sample supply chamber reaches the measuring chamber through the reagent melting/mixing means, and
    wherein, at least a portion of the sample received from the bypass passage is positioned for measurement and, thereafter, at least a portion of the sample received from the reagent melting/mixing means is positioned for measurement.

2. A sample measuring device according to claim 1, wherein one measuring chamber is configured to measure at least a portion of the sample received from the bypass passage and, thereafter, measure at least a portion of the sample received from the reagent melting/mixing means.

3. A sample measuring device, comprising:
    at least one reagent melting/mixing section;
    a sample supply chamber communicating with said reagent melting/mixing section to cause a sample to flow into said reagent melting/mixing section; and
    at least one measuring chamber communicating with said reagent melting/mixing section,
    wherein the sample supply chamber, said reagent melting/mixing section, and the measuring chamber are arranged from an upstream to a downstream side of a flow passage for a sample, which is moved by a sample moving section, and that the sample supply chamber is arranged on an upstream side of said reagent melting/mixing section, and the measuring chamber is arranged on a downstream side of said reagent melting/mixing section,
    wherein the reagent melting/mixing section comprises a reagent melting chamber accommodating a reagent that is to react with the sample and a mixing chamber communicating with the reagent melting chamber through a siphon,
    a bypass passage, connecting the sample supply chamber and the measuring chamber, bypassing at least one of the following components provided between the sample supply chamber and the measuring chamber: the reagent melting chamber, the mixing chamber, and the reagent melting/mixing means including the reagent melting chamber and the mixing chamber, and
    wherein, when an action force causing the sample to flow from the sample supply chamber to the measuring chamber is imparted to the sample measuring device, there is generated a time lag in sample inflow into the measuring chamber such that, as compared with the flow passage which allows the sample from the sample supply chamber to reach the measuring chamber though the reagent melting/mixing means, the flow passage which allows the sample to reach the measuring chamber through the bypass passage causes the sample to flow into the measuring chamber through the bypass passage before the sample from the sample supply chamber reaches the measuring chamber trough the reagent melting/mixing means, and wherein at least a portion of the sample received from the bypass passage is positioned for measurement and, thereafter, at least a portion of the sample received from the reagent melting/mixing section is positioned for measurement.

4. A sample measuring device according to claim 3, wherein a plurality of reagent melting/mixing sections communicate with each other though siphons.

5. A sample measuring device according to claim 3, wherein one measuring chamber is configured to measure at least a portion of the sample received from the bypass passage and, thereafter, measure at least a portion of the sample received from the reagent melting/mixing section.

6. A sample measuring device comprising:

at least one reagent melting/mixing means;

a sample supply chamber communicating with the reagent melting/mixing means to cause a sample to flow into the reagent melting/mixing means; and at least one measuring chamber communicating with the reagent melting/mixing means, wherein the sample supply chamber, the reagent melting/mixing means, and the measuring chamber are arranged from an upstream to a downstream side of a flow passage for a sample, which is moved by a sample moving means, and that the sample supply chamber is arranged on an upstream side of the reagent melting/mixing means, and the measuring chamber is arranged on a downstream side of the reagent melting/mixing means, wherein the reagent melting/mixing means comprises a reagent melting chamber accommodating a reagent that is to react with the sample and a mixing chamber communicating with the reagent melting chamber through a siphon, and wherein the reagent is a dried reagent which is prepared by applying a reagent to a film and drying it, a bypass passage, connecting the sample supply chamber and the measuring chamber, bypassing at least one of the following components provided between the sample supply chamber and the measuring chamber: the reagent melting chamber, the mixing chamber, and the reagent melting/mixing means including the reagent melting chamber and the mixing chamber, and wherein, when an action force causing the sample to flow from the sample supply chamber to the measuring chamber is imparted to the sample measuring device, there is generated a time lag in sample inflow into the measuring chamber such that, as compared with the flow passage which allows the sample from the sample supply chamber to reach the measuring chamber through the reagent melting/mixing means, the flow passage which allows the sample to reach the measuring chamber through the bypass passage causes the sample to flow into the measuring chamber through the bypass passage before the sample from the sample supply chamber reaches the measuring chamber through the reagent melting/mixing means, and wherein, at least a portion of the sample received from the bypass passage is positioned for measurement and, thereafter, at least a portion of the sample received from the reagent melting/mixing means is positioned for measurement.

7. A sample measuring device according to claim 6, wherein one measuring chamber is configured to measure at least a portion of the sample received from the bypass passage and, thereafter, measure at least a portion of the sample received from the reagent melting/mixing means.

8. A sample measuring device comprising:

at least one reagent melting/mixing means;

a sample supply chamber communicating with the reagent melting/mixing means to cause a sample to flow into the reagent melting/mixing means; and at least one measuring chamber communicating with the reagent melting/mixing means, wherein the sample supply chamber, the reagent melting/mixing means, and the measuring chamber are arranged from an upstream to a downstream side of a flow passage for a sample, which is moved by a sample moving means, and that the sample supply chamber is arranged on an upstream side of the reagent melting/mixing means, and the measuring chamber is arranged on a downstream side of the reagent melting/mixing means, and wherein when an action force causing the sample to flow from the sample supply chamber to the measuring chamber is imparted to the sample measuring device, there is generated a time lag in sample inflow into the measuring chamber such that, as compared with the flow passage which allows the sample from the sample supply chamber to reach the measuring chamber through the reagent melting/mixing means, the flow passage which allows the sample to reach the measuring chamber through a bypass passage, connecting the sample supply chamber and the measuring chamber causes the sample to flow into the measuring chamber through the bypass passage before the sample from the sample supply chamber reaches the measuring chamber through the reagent melting/mixing means, and wherein, at least a portion of the sample received from the bypass passage is positioned for measurement and, thereafter, at least a portion of the sample received from the reagent melting/mixing means is positioned for measurement.

9. A sample measuring device according to claim 8, wherein one measuring chamber is configured to measure at least a portion of the sample received from the bypass passage and, thereafter, measure at least a portion of the sample received from the reagent melting/mixing means.

10. A sample measuring device according to claim 8, further comprising a disposal chamber, and wherein liquid, which has passed through the bypass communication passage, enters the measuring chamber and the blank measurement is performed, and the liquid in the measuring chamber enters the disposal chamber, and then reagent melting liquid, which has passed through the melting/mixing means, enters the measuring chamber.

11. A sample measuring device according to claim 8, further comprising a siphon tubule, which extends along a reagent melting chamber of one of the at least one reagent melting/mixing means in the direction opposite to a centrifugal direction, turns back, at a position beyond the reagent melting chamber, to extend in the centrifugal direction.

12. A sample measuring device according to claim 8, further comprising at least one rib formed on a surface of the sample measuring device so that an inner side of a cover plate can be brought into press contact with an upper edge of the ribs.

13. A sample measuring device according to claim 8, wherein the at least one reagent melting/mixing means comprises a first reagent melting/mixing means and a second reagent melting/mixing means.

14. A sample measuring device according to claim 13, further comprising a first back-flow preventing chamber, a siphon tubule and a first passage,
    wherein the first back-flow preventing chamber communicates, through the siphon tubule, with the first reagent melting/mixing means and communicates, through the first passage, with an end, in a centrifugal direction, of a reagent melting chamber of the second reagent melting/mixing means.

15. A sample measuring device according to claim 13, further comprising a second back-flow preventing chamber and a third back-flow preventing chamber,
    wherein the at least one measuring chamber comprises a first measuring chamber and a second measuring chamber, and
    wherein a mixing chamber of the second reagent melting/mixing means communicates with the first measuring chamber and the second measuring chamber successively through a reverse-U-shaped tubule, the second back-flow preventing chamber, a second passage, and the third back-flow preventing chamber.

16. A sample measuring device comprising:
    at least one reagent melting/mixing means;
    a sample supply chamber communicating with the reagent melting/mixing means,
    wherein the sample supply chamber, the reagent melting/mixing means, and the passage for a sample, which is moved by a sample moving means, and that the sample supply chamber is arranged on an upstream side of the reagent melting/mixing means, and the measuring chamber is arranged on a downstream side of the reagent melting/mixing means; and
    wherein the at least one measuring chamber comprises at least two measuring chambers, one of the measuring chambers having a large cell length, and the other of the measuring chambers having a small cell length.

17. A sample measuring device according to claim 16, wherein one of the measuring chambers has a large depth, and the other of the measuring chambers has a small depth.

18. A sample measuring device according to claim 8, characterized in that the sample moving means is a centrifugal machine, and that, in use, the sample measuring device is installed in the centrifugal machine such that the sample supply chamber, the reagent melting/mixing means, and the measuring chamber are successively arranged along a radial direction of a rotor of the centrifugal direction and such that the sample supply chamber is situated on an inner side with respect to the radial direction of the rotor of the centrifugal machine.

19. A sample measuring device according to claim 8, characterized in that a plurality of reagent melting/mixing means communicate with each other through siphons.

20. A sample measuring device according to claim 8, characterized in that the sample moving means is a pressure generating means.

21. A sample measuring device according to claim 8, characterized in that there is provided a liquid flow control means equipped with a valve body and a means for detecting the sample.

22. A sample measuring device according to claim 8, characterized in that the flow passage is equipped with at least one back-flow preventing means.

23. A sample measuring device according to claim 8, characterized in that there are provided at least two of the measuring chambers, one of the measuring chambers is a measuring chamber communicating with the bypass passage and dedicated to sample blank measurement, and the other of the measuring chambers is a measuring chamber communicating with the sample supply chamber through the at least one reagent melting/mixing means.

24. A sample measuring device according to claim 8, characterized in that there are provided at least two of the measuring chambers, one of the measuring chambers is a measuring chamber with a large cell length, and the other of the measuring chambers is a measuring chamber with a small cell length.

25. A sample measuring device according to claim 8, characterized in that properties of a reaction sample flowing into the measuring chamber are measured by an optical measuring means or an electro-chemical measuring means.

26. A sample measuring device according to claim 8, characterized in that an air vent hole is provided at least in the reagent melting/mixing means.

27. A sample measuring device according to claim 8, further comprising an overflow chamber communicating with the measuring chamber, with the overflow chamber being situated on a downstream side of the chamber adjacent to and on an upstream side of the measuring chamber.

28. A sample measuring device according to claim 8, further comprising a disposal chamber communicating with the measuring chamber, with the disposal chamber being situated on a downstream side of the measuring chamber.

29. A sample measuring device according to claim 8, wherein a plurality of reagent melting/mixing means communicate with each other through siphons.

30. A sample measuring device according to claim 8, wherein the at least one reagent melting/mixing means comprises a first reagent melting/mixing means and a second reagent melting/mixing means.

31. A sample measuring device according to claim 30, further comprising a first back-flow preventing chamber, a siphon tubule and a first passage,
    wherein the first back-flow preventing chamber communicates, through the siphon tubule, with the first reagent melting/mixing means and communicates, through the first passage, with an end, in a centrifugal direction, of a reagent melting chamber of the second reagent melting/mixing means.

32. A sample measuring device according to claim 30, further comprising a second back-flow preventing chamber and a third back-flow preventing chamber,
    wherein the at least one measuring chamber comprises a first measuring chamber and a second measuring chamber, and
    wherein a mixing chamber of the second reagent melting/mixing means communicates with the first measuring chamber and the second measuring chamber successively through a reverse-U-shaped tubule, the second back-flow preventing chamber, a second passage, and the third back-flow preventing chamber.

33. A sample measuring device according to claim 8, further comprising a siphon tubule, which extends along a reagent melting chamber of one of the at least one reagent melting/mixing means in the direction opposite to a centrifugal direction, turns back, at a position beyond the reagent melting chamber, to extend in the centrifugal direction.

34. A sample measuring device according to claim 8, further comprising at least one rib formed on a surface of the sample measuring device so that an inner side of a cover plate can be brought into press contact with an upper edge of the ribs.

35. A sample measuring device according to claim 8, wherein the sample moving means is a pressure generating means, and wherein the sample measuring device is provided with a liquid flow control means equipped with a valve body and a means for detecting the sample.

* * * * *